(12) United States Patent
Touge et al.

(10) Patent No.: US 7,932,411 B2
(45) Date of Patent: Apr. 26, 2011

(54) METHOD FOR PRODUCING RUTHENIUM COMPLEX

(75) Inventors: Taichiro Touge, Hiratsuka (JP); Hideki Nara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 12/609,163

(22) Filed: Oct. 30, 2009

(65) Prior Publication Data

US 2010/0113814 A1    May 6, 2010

(30) Foreign Application Priority Data

Oct. 30, 2008 (JP) ................................. 2008-279858

(51) Int. Cl.
*C07F 15/00* (2006.01)

(52) U.S. Cl. ........................................................ 556/136

(58) Field of Classification Search .................... 556/136
See application file for complete search history.

(56) References Cited

OTHER PUBLICATIONS

Gupta et al., Organometallics, vol. 16, No. 20, pp. 4355-4361 (1997).*

Gao et al., Tetrahedron letters, vol. 49, No. 42, pp. 6126-6128 (2008).*

European Search Report dated Jan. 29, 2010, corresponding to European Application No. 09173619.9.

Bennett, et al., "Highly fluxional arene cyclooctatetraene complexes of zerovalent iron, ruthenium, and osmium. Single-crystal x-ray study of (cyclooctatetraene)(hexamethylbenzene) ruthenium(O), Ru(.eta.6HMB)(1-4.eta.-COT)", Inorg. Chem. 1980, 19, 1014-1021.

* cited by examiner

*Primary Examiner* — Porfirio Nazario Gonzalez
(74) *Attorney, Agent, or Firm* — Peter F. Corless; Dwight D. Kim; Edwards Angell Palmer & Dodge LLP

(57) ABSTRACT

The present invention provides a novel method for simply and efficiently producing a ruthenium aromatic complex which is suitable also as an industrial method. The production method includes reacting a ruthenium aromatic complex with an aromatic compound as a ligand of the ruthenium aromatic complex, In a sealed reaction container at a reaction temperature higher than the boiling point of the aromatic compound to produce a ruthenium aromatic complex having, as a ligand, an aromatic compound having a lower boiling point.

3 Claims, No Drawings

METHOD FOR PRODUCING RUTHENIUM COMPLEX

TECHNICAL FIELD

The present invention relates to a method for producing a ruthenium aromatic ring complex that is important as a precursor for the synthesis of catalysts, drugs, and functional materials.

BACKGROUND ART

A ruthenium aromatic ring complex as a ruthenium source having, as a ligand, a six-membered aromatic compound is used as a precursor for hydrogenation catalysts and complexes for hydrogen transfer. Further, in recent years, such a ruthenium aromatic ring complex has come to be used as a precursor for antitumor agents and thin film electrode materials for semiconductor devices, and therefore its demand is increasing.

A conventional method (i) for producing such a ruthenium aromatic ring complex is refluxing corresponding substituted 1,3- or 1,4-cyclohexadiene and ruthenium (III) trichloride trihydrate in ethanol or methanol (J. Chem. Soc., Dalton Trans (1974) p. 233).

Another conventional method (ii) for producing such a ruthenium aromatic ring complex is [RuCl$_2$(p-cymene)]$_2$ obtained by the method (i) and hexamethylbenzene or durene (1,2,4,5-tetramethylbenzene), which has a higher boiling point than p-cymene, were reacted at high temperature to exchange aromatic ring moieties (Inorg. Chem., 19(1980) p. 1014-1021 and Inorg. Synth., 21(1982) p. 74-78).

DISCLOSURE OF THE INVENTION

Problems to be Solved by the Invention

The substituted 1,3- or 1,4-cyclohexadiene used as a raw material in the conventional method (i) is generally obtained by subjecting a corresponding aromatic compound to reaction such as Birch reduction. Birch reduction is performed using liquid ammonia and metallic sodium or metallic lithium, and is therefore disadvantageous for industrial-scale application in that, for example, ultra-low temperature equipment is required for performing reaction and treatment of ammonia after reaction is not easy.

On the other hand, the conventional method (ii) absolutely requires an aromatic compound, which has a higher boiling point than p-cymene contained as an aromatic compound in a raw material complex [RuCl$_2$(p-cymene)]$_2$, to perform reaction, but such an aromatic compound that can be used for the reaction is very limited. Further, there is a strong possibility that an obtained complex itself will be decomposed because the reaction is performed at high temperature.

It is therefore an object of the present invention to provide a novel method for simply and efficiently producing a ruthenium aromatic ring complex which can be used also as an industrial production method.

Means for Solving the Problems

In order to achieve the object, the present inventors have extensively studied, and as a result, have found that a corresponding ruthenium aromatic ring complex can be obtained by heating and stirring, in a hermetically-sealed reaction container, a ruthenium aromatic ring complex, for example, an easily-available ruthenium aromatic ring complex [RuCl$_2$(p-cymene)]$_2$ and an aromatic compound whose boiling point is lower than that of p-cymene.

Accordingly, the present invention provides a method for producing a ruthenium complex represented by the following general formula (3):

$$[RuX_2(L^2)]_n \qquad (3)$$

(wherein Ru represents a ruthenium atom, X represents a halogen atom, L$^2$ represents an aromatic compound, and n is a natural number of 2 or more), the method including heating and stirring, in a hermetically-sealed reaction container, a ruthenium complex represented by the following general formula (1):

$$[RuX_2(L^1)]_n \qquad (1)$$

(wherein Ru represents a ruthenium atom, X represents a halogen atom, L$^1$ represents an aromatic compound, and n is a natural number of 2 or more) and an aromatic compound represented by the following general formula (2):

$$L^2 \qquad (2)$$

(wherein L$^2$ represents an aromatic compound whose boiling point is lower than that of L$^1$).

More specifically, the present invention provides the following (1) to (3).

(1) A method for producing a ruthenium complex represented by the following general formula (3):

$$[RuX_2(L^2)]_n \qquad (3)$$

(wherein Ru represents a ruthenium atom, X represents a halogen atom, L$^2$ represents an aromatic compound, and n is a natural number of 2 or more), the method including heating and stirring, in a hermetically-sealed reaction container, a ruthenium complex represented by the following general formula (1):

$$[RuX_2(L^1)]_n \qquad (1)$$

(wherein Ru represents a ruthenium atom, X represents a halogen atom, L$^1$ represents an aromatic compound, and n is a natural number of 2 or more) and an aromatic compound represented by the following general formula (2):

$$L^2 \qquad (2)$$

(wherein L$^2$ represents an aromatic compound whose boiling point is lower than that of L$^1$).

(2) The production method according to the above (1), wherein a boiling point of the aromatic compound represented by L$^1$ is from 80° C. to 250° C. at one atmosphere.

(3) The production method according to the above (1) or (2), wherein the ruthenium complex represented by the general formula (1) is [RuCl$_2$(p-cymene)]$_2$.

Effects of the Invention

According to the present invention, it is possible to provide a method for simply producing a ruthenium aromatic ring complex useful as an intermediate for hydrogenation catalysts etc. in good yield. The method according to the present invention does not cause environmental pollution, and is therefore suitable also as an industrial production method.

BEST MODE FOR CARRYING OUT THE INVENTION

Hereinafter, the present invention will be described in detail.

A method according to the present invention for producing a ruthenium complex represented by the following general formula (3):

includes reacting, in a hermetically-sealed container, a ruthenium complex represented by the following general formula (1):

with an aromatic compound represented by $L^2$ having a lower boiling point than $L^1$.

In the general formulas (1) and (3), X represents a halogen atom. Examples of the halogen atom include a chlorine atom, a bromine atom, and an iodine atom.

In the general formulas (1) and (3), $L^1$ and $L^2$ each represent an aromatic compound, and are not particularly limited as long as they have one or more six-membered aromatic rings. Preferred examples of such an aromatic compound include benzene derivatives represented by the following general formula (4).

[formula 1]

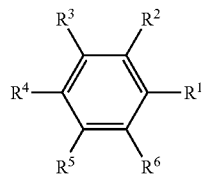

(4)

wherein $R^1$ to $R^6$ may be the same or different from each other and each represent a hydrogen atom, a saturated or unsaturated hydrocarbon group, an alkoxy group having 1 to 4 carbon atoms, a hydroxyalkyl group having 1 to 4 carbon atoms, or an alkoxycarbonyl group, and $R^1$ and $R^2$ may form together an alkylene chain which may have a substituent or an alkylenedioxy chain which may have a substituent.

The saturated hydrocarbon group represented by $R^1$ to $R^6$ is preferably an alkyl group having 1 to 6 carbon atoms. Specific examples of such an alkyl group include a methyl group, an ethyl group, an n-propyl group, an isopropyl group, an n-butyl group, an s-butyl group, an isobutyl group, a t-butyl group, an n-pentyl group, and an n-hexyl group.

The unsaturated hydrocarbon group represented by $R^1$ to $R^6$ is preferably an alkenyl or alkynyl group having 2 to 6 carbon atoms. Specific examples of such an alkenyl or alkynyl group include a vinyl group, an allyl group, a butenyl group, an ethynyl group, and a propargyl group.

Examples of the alkoxy group having 1 to 4 carbon atoms represented by $R^1$ to $R^6$ include a methoxy group, an ethoxy group, an n-propoxy group, an isopropoxy group, an n-butoxy group, an s-butoxy group, an isobutoxy group, and a t-butoxy group.

Examples of the hydroxyalkyl group having 1 to 4 carbon atoms represented by $R^1$ to $R^6$ include a hydroxymethyl group, a 1-hydroxyethyl group, a 2-hydroxyethyl group, a 3-hydroxypropyl group, and a 2-hydroxy-2-propyl group.

The alkoxycarbonyl group represented by $R^1$ to $R^6$ is, for example, an alkoxycarbonyl group having 2 to 5 carbon atoms. Specific examples of such an alkoxycarbonyl group include a methoxycarbonyl group, an ethoxycarbonyl group, a propoxycarbonyl group, and a butoxycarbonyl group.

The alkylene chain formed by $R^1$ and $R^2$ is an alkylene chain having 1 to 4 carbon atoms. Examples of such an alkylene chain include a methylene group, an ethylene group, a propylene group, and a trimethylene group. Examples of a substituent of the substituted alkylene chain include an alkyl group and a hydroxyl group.

Examples of the alkylenedioxy chain formed by $R^1$ and $R^2$ include groups each obtained by bonding an oxygen atom to each of the both ends of the alkylene chain described above.

Preferred examples of the aromatic compound represented by $L^1$ and $L^2$ include: benzene; alkyl-substituted benzenes such as p-cymene, toluene, o-xylene, m-xylene, p-xylene, mesitylene, hexamethylbenzene, ethylbenzene, cumene, and t-butylbenzene; unsaturated hydrocarbon group-substituted benzenes such as styrene, allylbenzene, and phenylacetylene; hydroxyalkyl group-substituted benzenes such as benzyl alcohol and phenethyl alcohol; alkoxy group-substituted benzenes such as anisole and ethoxybenzene; benzoate esters such as methyl benzoate and ethyl benzoate; indan; tetralin; and 2-indanol.

According to the method for producing a ruthenium aromatic ring complex of the present invention, a ruthenium aromatic ring complex can be produced by, for example, reacting $[RuCl_2(p\text{-cymene})]_2$ as a starting material with an aromatic compound represented by $L^2$ in a closed system such as an autoclave. The aromatic compound represented by $L^2$ is used in an amount of preferably 10 to 100 equivalents relative to a ruthenium atom. The aromatic compound represented by $L^2$ can be used also as a solvent. The reaction temperature is not particularly limited as long as it is equal to or higher than the boiling point of the aromatic compound represented by $L^2$, and is, for example, 100 to 250° C., preferably 150 to 250° C., more preferably 180 to 210° C.

The reaction time is 2 to 30 hours, preferably 4 to 20 hours. The production method according to the present invention is preferably performed in an inert gas such as nitrogen gas or argon gas.

After the completion of the reaction, a target complex can be very simply obtained by performing desired operations for separation such as filtration, concentration, and drying on a reaction mixture.

Hereinafter, the present invention will be described in more detail with reference to the following examples, but is not limited thereto. It is to be noted that in each of the following examples and comparative examples, identification and purity determination of a complex were performed by measuring the NMR spectrum of the complex by a Mercury Plus 300 4N spectrometer (300 MHz, internal standard material: tetramethylsilane) manufactured by Varian Technologies Japan Ltd.

As described in, for example, Angew. Chem. Int. Ed. Engl. 1997, 36, 318-320, a ruthenium aromatic ring complex obtained by the method according to the present invention can be converted into a ruthenium aromatic ring diamine complex by reaction with a diamine compound in a solvent such as an alcohol in the presence of a base.

Example 1

Synthesis of $[RuCl_2(\text{mesitylene})]_2$ 109.8 g (180 mmol) of $[RuCl_2(p\text{-cymene})]_2$ and 625 mL (4.5 mol) of mesitylene were placed in a hermetically-sealed autoclave and reacted in a nitrogen atmosphere at an internal temperature of 200° C. for 14 hours to obtain a reaction mixture. Then, the reaction mixture was cooled to room temperature, 400 mL of heptane was added to the reaction mixture, and the resulting mixture was cooled with ice and stirred. The mixture was further cooled to −20° C. to precipitate crystals, and the crystals were collected by filtration. The crystals were washed with 800 mL of heptane and then dried under a reduced pressure (133.32 Pa, 80° C.), and as a result, 100.7 g of a target complex [RuCl$_2$(mesitylene)]$_2$ with a purity of 99% was obtained in a yield of 96.0%.

$^1$H-NMR (DMSO-d$_6$) δ: 2.12 (s, CH$_3$), 5.44 (s, ArH)

Example 2

Synthesis of [RuCl$_2$(toluene)]$_2$ 20 g (32.7 mmol) of [RuCl$_2$(p-cymene)]$_2$ and 100 mL (940 mmol) of toluene were placed in a hermetically-sealed autoclave and reacted in a nitrogen atmosphere at a bath temperature of 200° C. for 7 hours to obtain a reaction mixture. Then, the reaction mixture was cooled to 5° C. to precipitate crystals, and the crystals were collected by filtration. The crystals were dried under a reduced pressure (133.32 Pa, 80° C.), and as a result, 14.9 g of a target complex [RuCl$_2$(toluene)]$_2$ with a purity of 99% was obtained in a yield of 88%.

$^1$H-NMR (DMSO-d$_6$) δ: 2.12 (s, CH$_3$), 5.68 (m, ArH), 5.97 (m, ArH)

Example 3

Synthesis of [RuCl$_2$(m-xylene)]$_2$ 20 g (32.7 mmol) of [RuCl$_2$(p-cymene)]$_2$ and 100 mL (818 mmol) of m-xylene were placed in a hermetically-sealed autoclave and reacted in a nitrogen atmosphere at a bath temperature of 190° C. for 6 hours to obtain a reaction mixture. Then, the reaction mixture was cooled to −15° C. to precipitate crystals, and the crystals were collected by filtration. The crystals were dried under a reduced pressure (133.32 Pa, 80° C.), and as a result, 17.3 g of a target complex [RuCl$_2$(m-xylene)]$_2$ with a purity of 99% was obtained in a yield of 98%.

$^1$H-NMR (DMSO-d$_6$) δ: 2.10 (s, CH$_3$), 5.41 (d, ArH), 5.59 (s, ArH), 5.96 (t, ArH)

Example 4

Synthesis of [RuCl$_2$(p-xylene)]$_2$ 3.05 g (5.0 mmol) of [RuCl$_2$(p-cymene)]$_2$ and 30.6 mL (250 mmol) of p-xylene were placed in a hermetically-sealed autoclave and reacted in a nitrogen atmosphere at a bath temperature of 200° C. for 18 hours to obtain a reaction mixture. Then, the reaction mixture was cooled to room temperature, 60 mL of hexane was added to the reaction mixture, and the resulting mixture was cooled with ice to 0° C. to precipitate crystals. The crystals were collected by filtration and then dried under a reduced pressure (133.32 Pa, 80° C.), and as a result, 2.58 g of a target complex [RuCl$_2$(p-xylene)]$_2$ with a purity of 100% was obtained in a yield of 93%.

$^1$H-NMR (DMSO-d$_6$) δ: 2.06 (s, CH$_3$), 5.74 (s, ArH)

Example 5

Synthesis of [RuCl$_2$(o-xylene)]$_2$ 3.05 g (5.0 mmol) of [RuCl$_2$(p-cymene)]$_2$ and 30.5 mL (250 mmol) of o-xylene were placed in a hermetically-sealed autoclave and reacted in a nitrogen atmosphere at a bath temperature of 200° C. for 19 hours to obtain a reaction mixture. Then, the reaction mixture was cooled to room temperature, 60 mL of hexane was added to the reaction mixture, and the resulting mixture was cooled with ice to 0° C. to precipitate crystals. The crystals were collected by filtration and then dried under a reduced pressure (133.32 Pa, 80° C.), and as a result, 2.30 g of a target complex [RuCl$_2$(o-xylene)]$_2$ with a purity of 89% was obtained.

$^1$H-NMR (DMSO-d$_6$) δ: 2.01 (s, CH$_3$), 5.71-5.78 (m, ArH)

Example 6

Synthesis of [RuCl$_2$(benzene)]$_2$ 3.05 g (5.0 mmol) of [RuCl$_2$(p-cymene)]$_2$ and 36 ml (450 mmol) of benzene were placed in a hermetically-sealed autoclave and reacted in a nitrogen atmosphere at a bath temperature of 200° C. for 17 hours to obtain a reaction mixture. Then, the reaction mixture was cooled to room temperature, 60 mL of hexane was added to the reaction mixture, and the resulting mixture was cooled with ice to 0° C. to precipitate crystals, and the crystals were collected by filtration. The crystals were dried under a reduced pressure (133.32 Pa, 80° C.), and as a result, 1.74 g of a target complex [RuCl$_2$(benzene)]$_2$ with a purity of 86% was obtained in a yield of 71%.

$^1$H-NMR (DMSO-d$_6$) δ: 5.94 (s, ArH)

Example 7

Synthesis of [RuCl$_2$(4-ethyltoluene)]$_2$ 500 mg (0.816 mmol) of [RuCl$_2$(p-cymene)]$_2$ and 5 ml of 4-ethyltoluene were placed in a hermetically-sealed autoclave and reacted in a nitrogen atmosphere at a bath temperature of 200° C. for 18 hours to obtain a reaction mixture. Then the reaction mixture was concentrated, hexane was added to the mixture and the resulting mixture was cooled with ice to 0° C. to precipitate crystals, and the crystals were collected by filtration. The crystals were dried under a reduced pressure (133.32 Pa, 80° C.), and as a result, 360 mg of a target complex [RuCl$_2$(4-ethyltoluene)]$_2$ with a purity of 70% was obtained in a yield of 75%.

$^1$H-NMR (CDCl$_3$) δ: 1.20-1.26 (t, CH$_2$CH$_3$), 2.18 (s, Ar—CH$_3$), 2.52-2.60 (q, CH$_2$CH$_3$), 5.32-5.40 (m, ArH)

Example 8

Synthesis of [RuCl$_2$(ethylbenzene)]$_2$

Other than using ethylbenzene instead of 4-ethyltoluene, the reaction was carried out in the same manner and using the same amount of reagent as in Example 7 and 320 mg of a target complex [RuCl$_2$(ethylbenzene)]$_2$ with a purity of 65% was obtained in a yield of 70%.

$^1$H-NMR (CDCl$_3$) δ: 1.12-1.26 (s, CH$_2$CH$_3$), 2.53-2.61 (q, CH$_2$CH$_3$), 5.37-5.40 (d, ArH), 5.55-5.58 (m, ArH), 5.64-5.68 (m, ArH)

Example 9

Synthesis of [RuCl$_2$(tert-butylbenzene)]$_2$

Other than using tert-butylbenzene instead of 4-ethyltoluene, the reaction was carried out in the same manner and using the same amount of reagent as in Example 7 and 410 mg of a target complex [RuCl$_2$(tert-butylbenzene)]$_2$ with a purity of 70% was obtained in a yield of 82%.

$^1$H-NMR (CDCl$_3$) δ: 1.40 (s, C(CH$_3$)$_3$), 5.60-5.64 (m, ArH), 5.67-5.69 (m, ArH), 5.82-5.84 (m, ArH)

Example 10

Synthesis of [RuCl$_2$(cumene)]$_2$

Other than using cumene (isopropyl benzene) instead of 4-ethyltoluene, the reaction was carried out in the same manner and using the same amount of reagent as in Example 7 and 380 mg of a target complex [RuCl$_2$(cumene)]$_2$ with a purity of 68% was obtained in a yield of 80%.

$^1$H-NMR (CDCl$_3$) δ: 1.25-1.27 (s, CH(C$\underline{H}_3$)$_2$), 2.90-2.94 (s, C$\underline{H}$(CH$_3$)$_2$), 5.45-5.47 (d, Ar$\underline{H}$), 5.57-5.60 (m, Ar$\underline{H}$), 5.63-5.67 (m, Ar$\underline{H}$)

Example 11

Synthesis of [RuCl$_2$(propylbenzene)]$_2$

Other than using propylbenzene instead of 4-ethyltoluene, the reaction was carried out in the same manner and using the same amount of reagent as in Example 7 and 310 mg of a target complex [RuCl$_2$(propylbenzene)]$_2$ with a purity of 58% was obtained in a yield of 65%.

$^1$H-NMR (CDCl$_3$) δ: 0.93-0.98 (t, CH$_2$CH$_2$C$\underline{H}_3$), 1.56-1.64 (m, CH$_2$C$\underline{H}_2$CH$_3$), 2.49-2.55 (t, C$\underline{H}_2$CH$_2$CH$_3$), 5.36-5.38 (d, Ar$\underline{H}$), 5.55-5.58 (m, Ar$\underline{H}$), 5.63-5.68 (m, Ar$\underline{H}$)

Example 12

Synthesis of [RuCl$_2$(indan)]$_2$

Other than using indan instead of 4-ethyltoluene, the reaction was carried out in the same manner and using the same amount of reagent as in Example 7 and 402 mg of a target complex [RuCl$_2$(indan)]$_2$ with a purity of 70% was obtained in a yield of 85%.

$^1$H-NMR (CDCl$_3$) δ: 1.99-2.02 (m, —CH$_2$C$\underline{H}_2$CH$_2$—), 2.31-2.33 (m, —C$\underline{H}_2$CH$_2$CH$_2$—), 2.31-2.37 (m, —CH$_2$CH$_2$C$\underline{H}_2$—), 2.88-2.93 (m, —C$\underline{H}_2$CH$_2$C$\underline{H}_2$—), 5.53-5.60 (m, Ar$\underline{H}$)

Comparative Example 1

Reaction for Conversion from [RuCl$_2$(p-cymene)]$_2$ into [RuCl$_2$(mesitylene)]$_2$ 2.2 g (3.6 mol) of [RuCl$_2$(p-cymene)]$_2$ and 12.5 mL (90.0 mmol) of mesitylene were mixed in a two-necked flask equipped with a reflux condenser and reacted under reflux at atmospheric pressure and at a bath temperature of 200° C. and an internal temperature of 155° C. for 17 hours to obtain a reaction mixture. Then, the reaction mixture was cooled to room temperature, 20 mL of hexane was added to the reaction mixture, and the resulting mixture was cooled with ice to 0° C. to precipitate crystals. The crystals were collected by filtration and then dried under a reduced pressure (133.32 Pa, 80° C.) to obtain a reaction product. The reaction product was analyzed by $^1$H-NMR, and as a result, it was found that the rate of conversion into a target complex [RuCl$_2$(mesitylene)]$_2$ was about 25%.

Comparative Example 2

Reaction for Conversion from [RuCl$_2$(p-cymene)]$_2$ into [RuCl$_2$(mesitylene)]$_2$ 2.2 g (3.6 mol) of [RuCl$_2$(p-cymene)]$_2$ and 12.5 mL (90.0 mmol) of mesitylene were mixed in a two-necked flask equipped with a reflux condenser and reacted under reflux at atmospheric pressure and at a bath temperature of 200° C. and an internal temperature of 155° C. for 24 hours to obtain a reaction mixture. Then, the reaction mixture was cooled to room temperature, 20 mL of hexane was added to the reaction mixture, and the resulting mixture was cooled with ice to 0° C. to precipitate crystals. The crystals were collected by filtration and then dried under a reduced pressure (133.32 Pa, 80° C.) to obtain a reaction product. The reaction product was analyzed by $^1$H-NMR, and as a result, it was found that the rate of conversion into a target complex [RuCl$_2$(mesitylene)]$_2$ was about 25%.

Comparative Example 3

Reaction for Conversion from [RuCl$_2$(p-cymene)]$_2$ into [RuCl$_2$(mesitylene)]$_2$ 0.87 g (1.42 mol) of [RuCl$_2$(p-cymene)]$_2$ and 50.0 mL (416 mmol) of mesitylene were mixed in a two-necked flask equipped with a reflux condenser and reacted under reflux at atmospheric pressure and at a bath temperature of 200° C. and an internal temperature of 155° C. for 24 hours to obtain a reaction mixture. Then, the reaction mixture was cooled to room temperature, 50 mL of hexane was added to the reaction mixture, and the resulting mixture was cooled with ice to 0° C. to precipitate crystals. The crystals were collected by filtration and then dried under a reduced pressure (133.32 Pa, 80° C.) to obtain a reaction product. The reaction product was analyzed by $^1$H-NMR, and as a result, it was found that the rate of conversion into a target complex [RuCl$_2$(mesitylene)]$_2$ was about 61%.

Reference Example 0.76 mL (5.46 mmol) of triethylamine and 26 mL of 2-propanol were added to 0.72 g (1.36 mol) of [RuCl$_2$(toluene)]$_2$ and 1.0 g (2.73 mmol) of (1R,2R)—N-p-toluenesulfonyl ethylenediamine (hereinafter, referred to as (R,R)-TsDPEN), and they were heated and stirred at 80° C. for 1 hour to obtain a reaction solution. Then, the solution was cooled and then concentrated to precipitate crystals. The crystals were collected by filtration, washed with a small amount of water, and dried under a reduced pressure. As a result, 1.5 g (yield: 88%) of brownish white crystals of RuCl[(R,R)-TsDPEN] (toluene) was obtained.

In the same manner as described above, yellow crystals of RuCl[(R,R)-TsDPEN] (m-xylene) were obtained in an yield of 82%, and orange crystals of RuCl[(R,R)-TsDPEN] (p-xylene) were obtained in an yield of 93%.

INDUSTRIAL APPLICABILITY

The present invention provides a method for simply and efficiently producing an industrially useful ruthenium aromatic ring complex and has industrial applicability.

The invention claimed is:

1. A method for producing a ruthenium complex represented by the following general formula (3):

[RuX$_2$(L$^2$)]$_n$     (3)

(wherein Ru represents a ruthenium atom, X represents a halogen atom, L$^2$ represents an aromatic compound, and n is a natural number of 2 or more), the method comprising heating and stirring, in a hermetically-sealed reaction container, a ruthenium complex represented by the following general formula (1):

[RuX$_2$(L$^1$)]$_n$     (1)

(wherein Ru represents a ruthenium atom, X represents a halogen atom, $L^1$ represents an aromatic compound, and n is a natural number of 2 or more) and an aromatic compound represented by the following general formula (2):

$$L^2 \tag{2}$$

(wherein $L^2$ represents an aromatic compound whose boiling point is lower than that of $L^1$).

2. The production method according to claim 1, wherein a boiling point of the aromatic compound represented by $L^1$ is from 80° C. to 250° C. at one atmosphere.

3. The production method according to claim 1 or 2, wherein the ruthenium complex represented by the general formula (1) is $[RuCl_2(p\text{-cymene})]_2$.

* * * * *